US011826280B2

(12) United States Patent
Barnett et al.

(10) Patent No.: US 11,826,280 B2
(45) Date of Patent: Nov. 28, 2023

(54) LACRIMAL CANALICULAR DELIVERY SYSTEM AND METHODS OF USE

(71) Applicant: THE JOHNS HOPKINS UNIVERSITY, Baltimore, MD (US)

(72) Inventors: Bradley P. Barnett, Apex, NC (US); Albert S. Jun, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 109 days.

(21) Appl. No.: 17/265,648

(22) PCT Filed: Jul. 15, 2019

(86) PCT No.: PCT/US2019/041790
§ 371 (c)(1),
(2) Date: Feb. 3, 2021

(87) PCT Pub. No.: WO2020/028022
PCT Pub. Date: Feb. 6, 2020

(65) Prior Publication Data
US 2021/0298950 A1 Sep. 30, 2021

Related U.S. Application Data

(60) Provisional application No. 62/714,219, filed on Aug. 3, 2018.

(51) Int. Cl.
*A61F 9/00* (2006.01)
(52) U.S. Cl.
CPC .................. *A61F 9/0017* (2013.01)
(58) Field of Classification Search
CPC ........ A61F 9/0017; A61F 9/0008; A61F 9/00; A61F 9/0026; A61F 9/007; A61F 9/00736; A61F 9/00772; A61F 9/00781; A61F 2/95; A61F 2009/00891; A61F 2/167; A61M 31/002; A61M 27/002; A61M 2210/0612; A61M 2005/206; A61M 31/007; A61M 37/0069; A61P 9/00
See application file for complete search history.

(56) References Cited

U.S. PATENT DOCUMENTS

| 4,733,802 | A | * | 3/1988 | Sheldon | ................ A61F 9/0026 604/302 |
| 4,994,028 | A | * | 2/1991 | Leonard | ............ A61M 37/0069 604/59 |
| 5,534,007 | A | | 7/1996 | St. Germain et al. | |
| 5,647,857 | A | | 7/1997 | Anderson et al. | |
| 6,059,813 | A | | 5/2000 | Vrba et al. | |

(Continued)

FOREIGN PATENT DOCUMENTS

WO 2017040855 A1 3/2017
WO 2017201255 A1 11/2017

*Primary Examiner* — Nicholas J. Weiss
*Assistant Examiner* — Brandon W. Levy
(74) *Attorney, Agent, or Firm* — JOHNS HOPKINS TECHNOLOGY VENTURES

(57) ABSTRACT

Lacrimal canalicular delivery systems (LCDS) and their methods of use for the delivery of implants at a specific location into the canaliculus of a subject generally include a lumen, a guide wire, and an implant. The guide wire and implant are within the lumen. When pressure is applied to the guide wire, the guide wire pushes the implant out of the lumen into a specific location into the canaliculus of a subject.

10 Claims, 11 Drawing Sheets

(56) References Cited

U.S. PATENT DOCUMENTS

| | | | |
|---|---|---|---|
| 6,352,561 B1 | 3/2002 | Leopold et al. | |
| 6,447,540 B1 | 9/2002 | Fontaine et al. | |
| 9,155,656 B2 * | 10/2015 | Schaller | A61F 9/00781 |
| 2012/0271272 A1 * | 10/2012 | Hammack | A61M 5/486 |
| | | | 604/257 |
| 2013/0158561 A1 * | 6/2013 | Bhagat | A61F 9/0017 |
| | | | 606/107 |

* cited by examiner

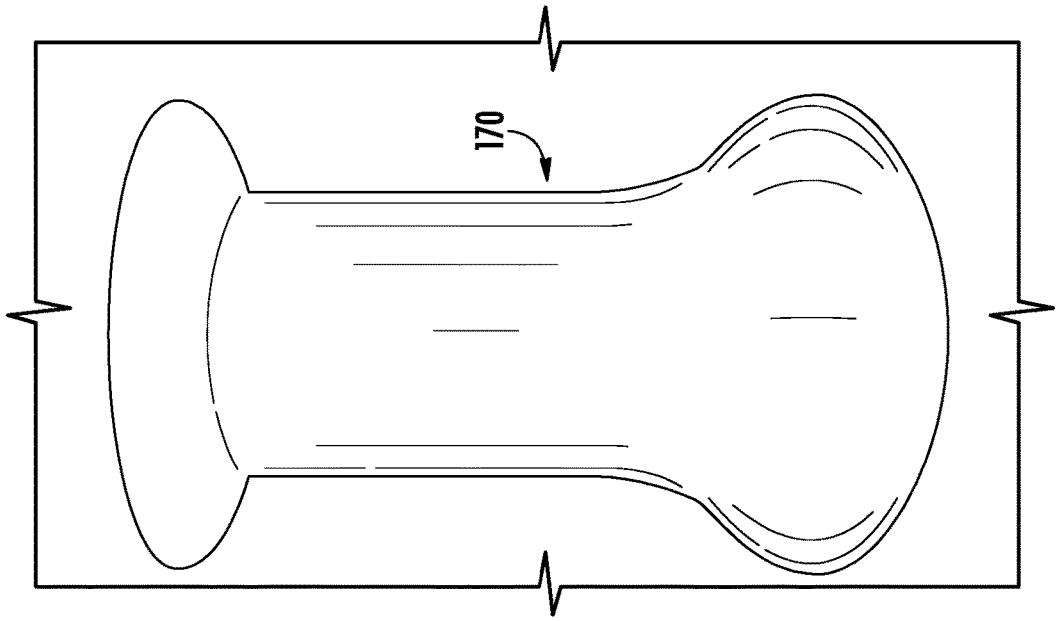
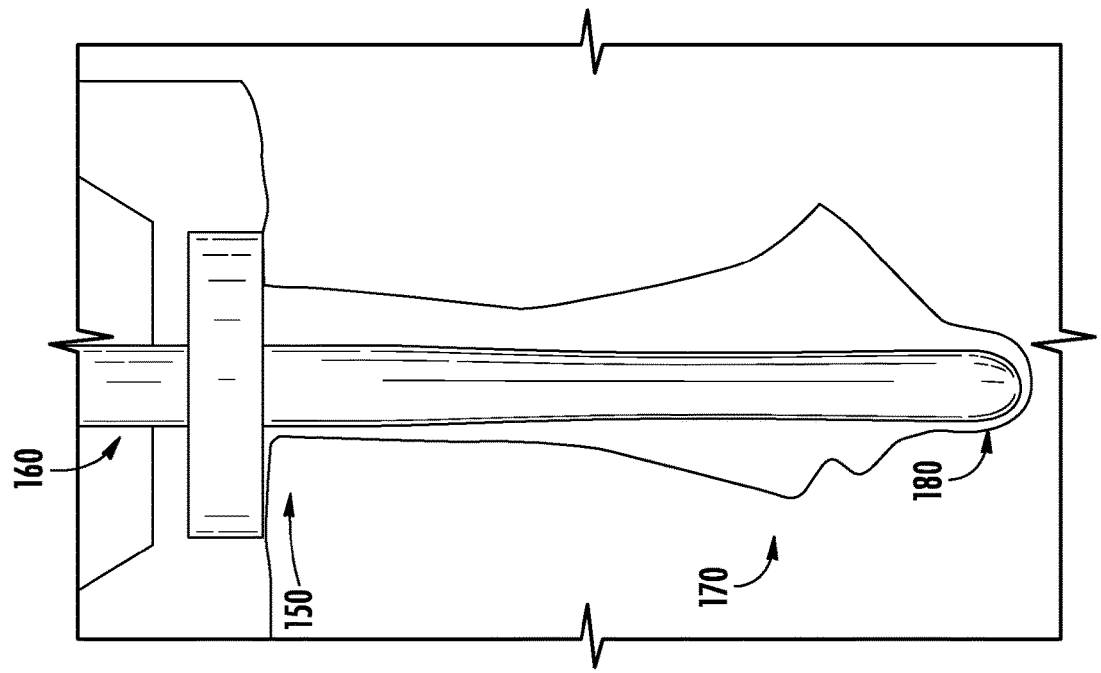

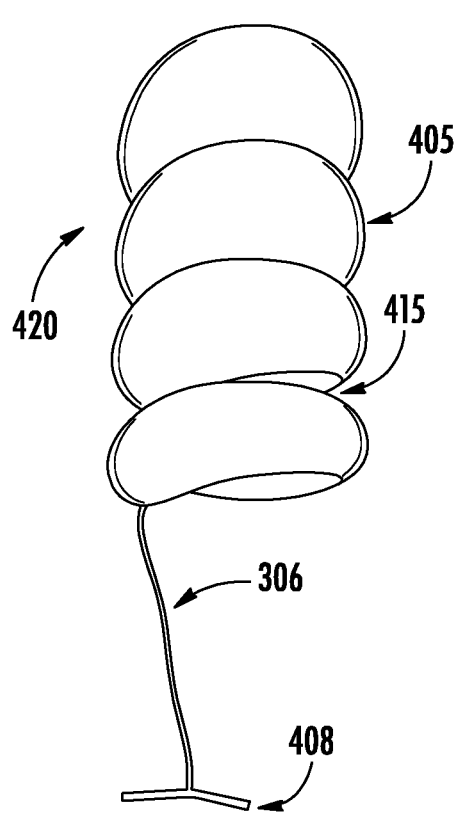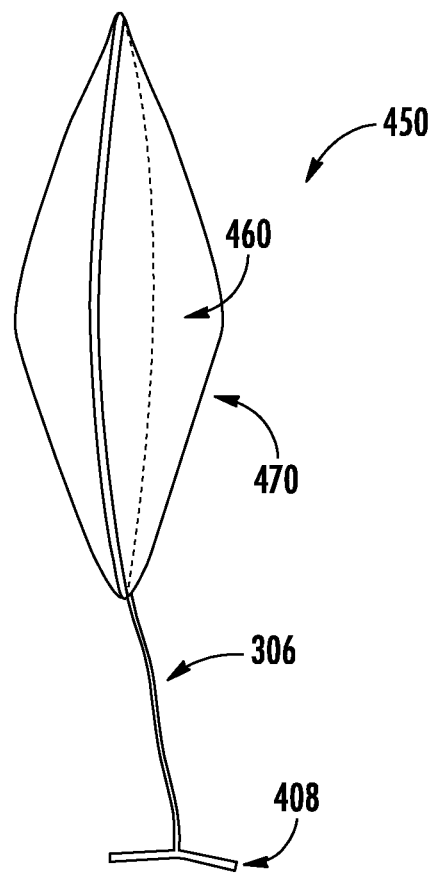
FIG. 4A                    FIG. 4B

LACRIMAL CANALICULAR DELIVERY SYSTEM AND METHODS OF USE

CROSS-REFERENCE TO RELATED APPLICATIONS

This application is a 35 U.S.C. § 371 U.S. national entry of International Application PCT/US2019/041790 having an international filing date of Jul. 15, 2019, which claims the benefit of U.S. Provisional Application No. 62/714,219, filed Aug. 3, 2018, the content of each of the aforementioned applications is herein incorporated by reference in their entirety.

BACKGROUND OF THE INVENTION

With the advent of novel depot drug delivery implants and tear drainage occlusion devices designed to be delivered in the canalicular space, the need for devices to deliver said implants arise. An ideal lacrimal canalicular delivery system (LCDS) could be universally used in any canalicular system and enable precision delivery at an appropriate depth in the canalicular space in a manner that is both safe and comfortable for the patient as well as easy to use by the end-user. To this end, the subject of this invention is a novel LCDS and the associated methods of use.

Unlike the cardiovascular field, which is replete with examples of intravascular delivery devices, the lacrimal canalicular system is a relatively unprobed space. Current delivery devices consist of a simple mechanism to facilitate entry of the canalicular implant in through the punctal os. After introduction into the os, it is then dependent on the end user to advance the device to the proper depth into the canalicular system thereby enabling deployment of the implant at the desired location. At the slit lamp, this task can prove non-exact and punctal plugs may be inadvertently placed too deep within the canalicular system. In certain instances, this complication requires surgical intervention to recover the implant. In the case of nasolacrimal tubes for nasolacrimal duct obstruction, introduction is almost routinely done in the operating room in part due to difficulty of manually threading a tube through the canalicular space.

A need exists clinically, for a class of devices to provide minimally invasive deployment in the canalicular space beyond a simple introducer. These LCDS, ideally would enable the ease and precision of device deployment that is seen in the vascular space. Device deployment in the vascular space is almost entirely guided with x-ray fluoroscopy to achieve the proper deployment depth. As ophthalmologists do not routinely use x-ray fluoroscopy, and radioactive exposure to the eye and CNS should be avoided unless clinically essential, a means of enabling precise deployment depth without image-guidance is needed.

In U.S. Pat. No. 6,352,561, issued to Leopold et al., a sheath is formed around an expandable endoluminal device and a control line used to maintain the sheath around the endoluminal device. The sheath is formed by folding a length of polymeric material in half and stitching the opposing edges together with the control line. The stitching pattern permits the control line to be removed from the sheath by pulling on a proximal end of the control line. As the control line becomes unstitched from the sheath, the endoluminal device is progressively released from confinement within the sheath. The control line is removed from the assembly as a distinct entity while the sheath remains at the implantation site.

In U.S. Pat. No. 5,647,857, issued to Anderson et al., an endoluminal device is held in a collapsed configuration over a catheter by a sheath. The assembly is provided with a control line having a free end and an end attached to a collar component of the catheter. The sheath is removed from the endoluminal device by pulling on the control line. As the control line is pulled, it cuts through and splits the sheath material from intracanalicular element to proximal end. As the sheath splits open, the endoluminal device is freed to expand. Unlike Leopold et al., the control line remains mechanically attached to the sheath and catheter assembly following deployment of the endoluminal device.

In U.S. Pat. No. 6,447,540, issued to Fontaine et al., a confining sheath is removed from around an endoluminal device with a control line that cuts through and splits the sheath material when pulled by a practitioner, much like Anderson et al. As with Leopold et al, the control line can be completely removed from the assembly as a distinct entity.

In U.S. Pat. No. 5,534,007, issued to St. Germain et al., a single-walled sheath that can collapse and shorten along its length is placed around a stent. As the distal portion of the sheath is retracted, it uncovers the stent. The uncovered stent is free to expand. A control line can be used to exert a pulling force on the collapsible sheath as a means of removing the sheath from the stent. The control line remains attached to the sheath during and subsequent to deployment of the stent.

In U.S. Pat. No. 6,059,813, issued to Vrba et al, a double-walled confinement sheath for an endoluminal device is described. In an assembly made of these components, the endoluminal device is placed over a catheter shaft in a collapsed configuration. An outer tube is placed in slidable relationship over the catheter. The intracanalicular element of the outer tube does not extend to cover the endoluminal device. Rather, the double walled sheath is placed over the collapsed endoluminal device. The inner wall of the sheath is attached to the catheter shaft near the proximal end of the endoluminal device. The outer wall of the double-walled sheath is mechanically attached to the outer tube. Movement of the outer tube relative to the catheter causes the outer wall of the sheath to move past the inner wall of the sheath. Movement of the outer tube in the proximal direction causes the sheath to retract and uncover the underlying endoluminal device. As the sheath retracts, the endoluminal device becomes free to expand. A control line is mechanically attached to the outer tube and serves to move the outer tube and retract the sheath.

SUMMARY OF THE INVENTION

Lacrimal Canalicular Delivery Systems (LCDS) with an integrated eyelid alignment platform that allows precision device depth deployment without image-guidance have been developed The end-user simply threads an implant held in a collapsed position within a catheter, or held constrained by other mechanisms herein described. The catheter can then be threaded into the punctal os until the eyelid alignment platform is appropriately positioned on the eyelid. This process could potentially be done at the slit-lamp or even without minimal visual guidance. By simply introducing the catheter into the punctal os and then threading the catheter to the appropriate depth so the upside-down saddle-shaped eyelid alignment platform rests on the eyelid margin, the end-user has ensured the catheter has been introduced at the predetermined depth. With a mechanical one button deployment mechanism, the catheter retracts beyond the eyelid alignment platform into the handle of the device, thereby allowing expansion of the canalicular device at the appropriate location.

One embodiment of the present invention are lacrimal canalicular delivery systems (LCDS). An LCDS comprises a lumen, a guide wire, and an implant. The guide wire and implant are positioned within the lumen and when pressure is applied to the guide wire, the guide wire pushes the implant out of the lumen into the canaliculus of a subject. Suitable implants fit within the lumen of a LCDS of the present invention and include a canalicular occlusive device, an endoluminal device, an electric stimulation device, a depot drug delivery device, a drug, or a combination thereof, as examples.

Another embodiment of the present invention is a lacrimal canalicular delivery system having a different configuration than the one described above. This LCDS comprises a handle connected to a catheter and a sheath through which the catheter moves. Sandwiched between the catheter and the sheath is a spring and the spring is distally attached to the portion of the handle contiguous with an eyelid alignment platform. The proximal portion of the spring is attached to the proximal element of the catheter and the catheter is open when the spring is maximally compressed. The catheter is retracted when the spring is maximally expanded.

Another embodiment of the present invention is a method of delivering an implant to a canaliculus of a subject. The method includes the steps of providing a lacrimal canalicular delivery system of the present invention. Administering the implant into the canaliculus of a subject by applying force to the guide wire. The guidewire extends through the punctal os into the canaliculus of the subject and the implant is released into a subject's canaliculus. Suitable implants used in the methods of the present invention include a canalicular occlusive device, an endoluminal device, an electric stimulation device, a depot drug delivery device, a drug, or combinations thereof, as examples. An implant placed in a canaliculus may deliver a pharmaceutical agent. In addition, any of the implants used in the present invention may be released at a specified location in a canaliculus. For example, an implant delivering a pharmaceutical agent may be released close to the punctal os to allow a pharmaceutical agent to elute in the tears of a subject. Other times an implant delivering a pharmaceutical agent is released deep in the canaliculus so that the pharmaceutical agent is prevented from eluting in the tears of a subject.

Another embodiment of the present invention is a method of delivering an implant to a canaliculus of a subject. This method comprises the steps of providing a lacrimal canalicular delivery system of the present invention. Aligning the eyelid alignment platform of a LCDS on the lid of a subject over the punctal os. Administering the implant into the canaliculus of a subject by applying force to the catheter. The catheter extends through the punctal os into the canaliculus of the subject and the implant is released into the lacrimal canaliculus when the catheter is retracted.

Definitions

The term "distal" refers anatomically to the region deep within a canalicular system. When referring to a device of the present invention "distal" refers to the portion of the device (such as occlusive element in the shape of a cap 302 shown in FIG. 2, as an example) that is intended to be inserted and deployed deep within the canalicular system.

The term "proximal" refers anatomically from within the canalicular system towards the punctum and external to the patient. When referring to a device of the present invention it represents the portion of the delivery device near a fixation element (such as a fixation element in the shape of arms 308 in FIG. 2 or a fixation element in the shape of a loop 408 FIG. 3).

The term "reduces" refers to a negative alteration of at least 10%, 25%, 50%, 75%, or 100%.

The term "reference" refers to a standard or control conditions such as a sample (punctum) or a subject that is a free, or substantially free, of a device of the present invention.

The term "subject" is intended to refer to any individual or patient to which the method described herein is performed. Generally, the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptom associated therewith such as dry eye disease. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

As used herein, the terms "prevent," "preventing," "prevention," "prophylactic treatment" and the like refer to reducing the probability of developing a disorder or condition in a subject, who does not have, but is at risk of or susceptible to developing a disorder or condition such as dry eye, for example.

BRIEF DESCRIPTION OF THE DRAWINGS

FIG. 1 illustrates an example of a conventional stretch plug design.

FIG. 4A-4B illustrates alternate designs of the canalicular occlusion device of the present invention.

DETAILED DESCRIPTION OF THE INVENTION

Canalicular Occlusion Devices

Figure 2:
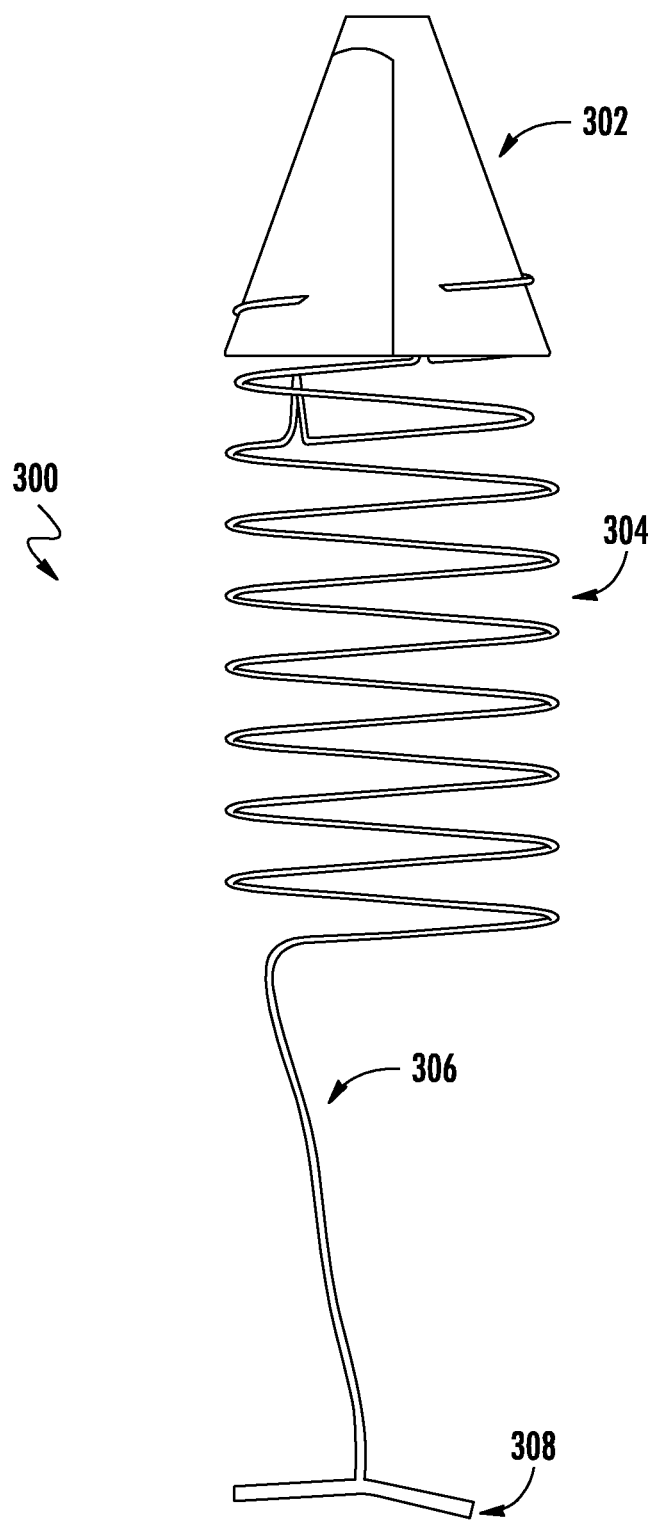
FIG. 2 illustrate an example of a canalicular occlusion device design of the present invention.

The inventors discovered a self-expanding lacrimal canalicular occlusion device designed to be a one-size fits all. The occlusion device may be used for occlusion of the canalicular anatomy as a treatment for eye diseases including dry eyes. Examples of canalicular occlusion devices of the present invention are provided in FIGS. 2 and 4. FIG. 2 shows a helical shaped occlusion device 300 wherein the occlusive element 302 and the memory frame 304 are in the shape of a helix. The linear frame 306 is linear, and the fixation element is in the shape of arms 308. FIGS. 4A and 4B illustrate additional examples of canalicular occlusion device designs. In FIG. 4A, an occlusive device with a spiral occlusive membrane 405 is illustrated. An occlusive element having a spiral shape 405 covers a memory frame 415 that extends into the occlusive element. The occlusive device includes a linear frame 306 and fixation elements in the shape of arms 408. In FIG. 4B, an occlusion device in the shape of a football 450 is illustrated. The occlusive element has a football shape when in an expanded form 450 (expanded form is shown). The occlusion element 470 covers or surrounds a memory frame 460. In some embodiments, an occlusion element includes a linear frame 306 and a fixation element in the shape of arms 408.

All, or some of, the elements of a canalicular occlusion device of the present invention may comprise memory material metal, such as a memory frame. Suitable memory material metals (a memory material) include stainless steel, cobolt, nickel, chromium, molybdenumtitanium, Nitinol, tantalum, platinum-iridium alloy, gold, magnesium, MP35N, MP20N, or combinations "MP35N" consists of 35% cobalt, 35% nickel, 20% chromium, and 10% molybdenum. "MP20N" consists of 50% cobalt, 20% nickel, 20% chromium, and 10% molybdenum. All, or some of, the elements of a canalicular occlusion device of the present invention may comprise a memory polymer. Memory polymers suitable for use in the present invention includes polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and blends thereof. Memory metals and or memory polymers used in the present invention may be covered in a biocompatible membrane. Suitable biocompatible polymers include poly(ethylene terephthalate), polylactide, polyglycolide and copolymers thereof; fluorinated polymers, such as PTFE, expanded PTFE and poly(vinylidene fluoride); polysiloxanes, including potydimethyl siloxane; and polyurethanes, including polyetherurethanes, polyurethane ureas, polyetherurethane ureas, polyurethanes containing carbonate linkages and polyurethanes containing siloxane segments.

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably, the porous sheet is made of one or more polymers that do not require treatment or modification to be biocompatible. The graft material may include a biocompatible polyurethane. Examples of biocompatible polyurethanes include THORALON™ (Thoratec, Pleasanton, Calif.), BIOSPAN™, BIONATE$^\beta$, ELASTHANE™, PURSIL™ and CARBOSIL™ (Polymer Technology Group, Berkeley, Calif.). A biocompatible polymer used in the present invention may have a Young's modulus in the range of 0.01 kPa to 1 kPA.

Figure 3:
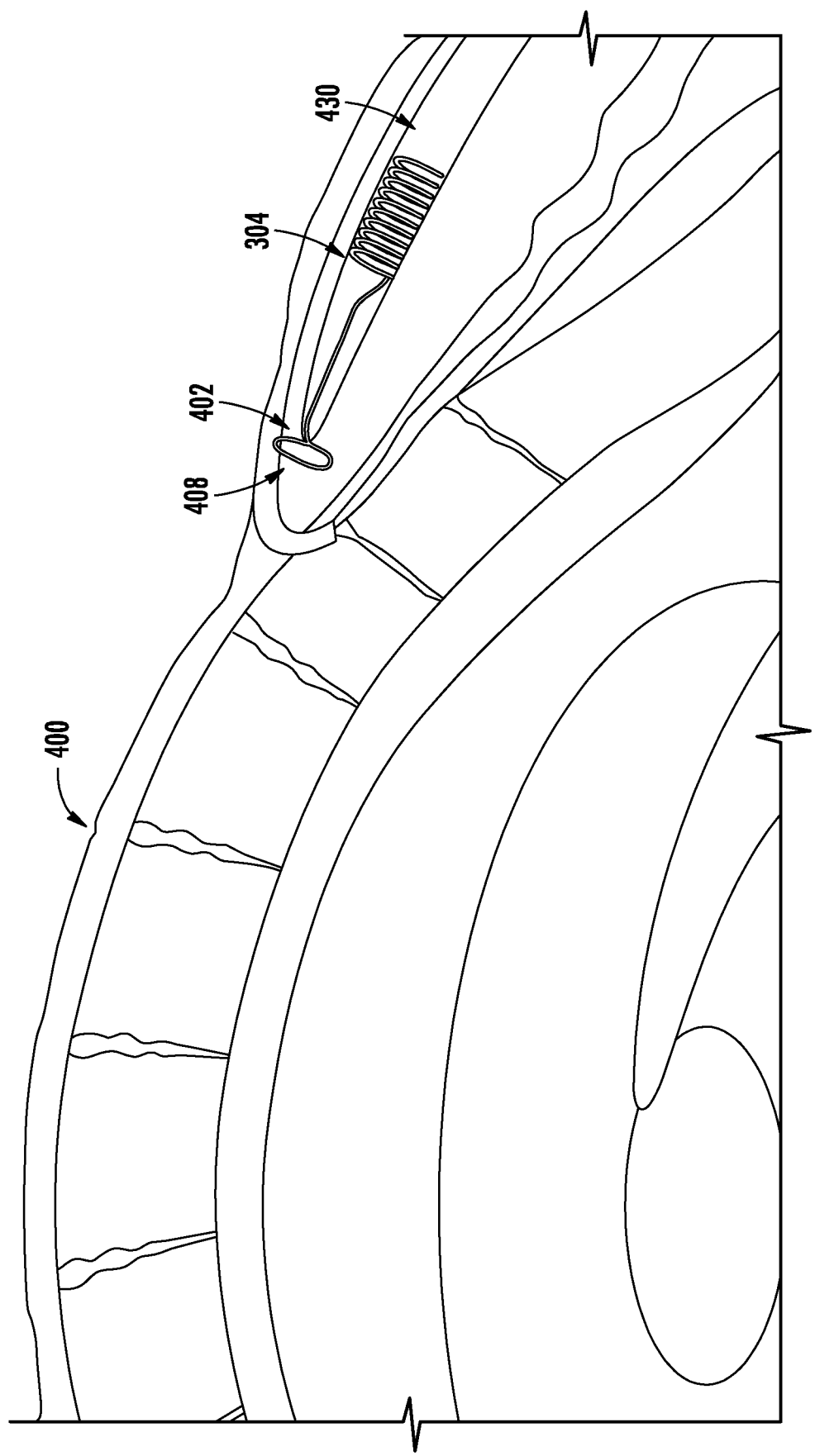
FIG. 3 illustrates an example of a canalicular occlusion device within the canaliculus of a subject.

The canalicular occlusion devices of the present invention are collapsible and stretchable to be comfortably inserted into canalicular anatomy using a low-profile delivery device. The canalicular occlusion device is stretched by a low profile delivery device, so that it becomes narrow, almost linear prior to delivery of the canalicular occlusion device to a subject (i.e. constrained form). When the delivery device retracts, the helix is free to expand to its native shape (i.e. expanded form) based upon its predetermined shape as shown in FIG. 3. FIG. 3 illustrates a picture of an eye including a cornea 400 a punctum 402 and a canaliculus 430. An occlusion device of the present invention, in an expanded form, is located in the canaliculus with a fixation element in the shape of a loop 408 located outside the canaliculus. The memory frame in the shape of a helix 304 is located in the canaliculus. Ideally, the memory frame in the shape of a helix 304 expands to durably occlude the canaliculus without creating undue pressure on the canalicular walls so as to avoid canalicular trauma and dilatation. As the canaliculi measure 8-10 mm in length and 0.5-1.0 mm in diameter the ideal canalicular occlusion device design would fall within or just beyond these bounds, for example between 5-12 mm in length and 0.3 and 2.0 mm in width. Longer designs could be employed to occlude the common canaliculus to provide occlusion of the upper and lower punctum with a single device.

The geometry of a human canalicular system will dictate the optimal design of the occlusion element and/or memory frame. In an ideal embodiment, a memory frame and/or occlusion element would enlarge to occupy all potential canalicular anatomy. Specifically, it would provide a sufficient radial force in the largest canalicular segment to provide durable occlusion and stable positioning while not providing too great of outward radial force to damage the smallest canalicular segment. A canalicular occlusion device of the present invention may be in the range of size from 0.1 mm to 1 mm. Unrestrained the diameter of coil would likely be 1 mm.

Occlusive Element

An occlusion element of the present invention may have a variety of shapes including spiral, football, box, etc. and is located at the distal end of a canalicular occlusion device. An occlusion element is held in position by the memory frame that is connected to the occlusion element and is responsible for converting the occlusion element from a constrained form to an expanded form. An occlusion membrane may be attached to the frame according to techniques known by those skilled in the art such as with an adhesive. The adhesive may be a thermoplastic adhesive and more preferably may be a thermoplastic fluoropolymer adhesive such as fluorinated ethylene propylene (hereinafter FEP) or perfluoroalkoxy (hereinafter PFA). In some embodiments, the occlusive element may comprise first and second tubular coverings. When such an occlusive element is expanded, the tubular coverings are affixed to each other through the multiplicity of openings in the stent wall. The two coverings may be affixed by heating them above the crystalline melt point of a polymer they are made of, such as that of PTFE film, to adequately cause them to thermally adhere. Alternatively, an adhesive such as FEP may affix them. In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching. Occlusive elements are made of occlusive element materials. Suitable occlusive element materials including polytetrafluoroethylene, polyethylene terephthalate, polyethylene, silicone, acrylate polymer, urethane polymer, rayon, rubber, latex, polyurethane, thermoplastic polyurethane, polyvinylchloride, and a combinations of the above, as examples, and or coating of said materials on other natural or other synthetic fabrics in order to achieve a waterproof membrane Fixation Element A fixation element is located preferably on the most proximally on a canalicular occlusion device and is designed to be delivered within punctal os in order to prevent migration and enable retrieval. The shape of said arms can be modified to a variety of shapes in order to improve ease of recovery, comfortability, and stability. A fixation element may be a wire coated with a layer of PTFE. Fixation element designed strategies include T arms, S arms, loops, helix, coil, Y shape, golf tee, and sphere shapes, as example. A symmetrical fixation element design such as a coil or S may be preferred as compared to a T design to enable precise alignment along an eyelid margin of a subject. For example, a circular shape fixation element can be deployed in any orientation 360 in relation to punctal os whereas a fixation element have arms in the shape of a T wherein the arms are oriented towards and away from eye may prove uncomfortable and potentially harmful to eye if extension is beyond the lid margin. In order to prevent inward migration, as well as to enable ease of removal, a fixation element emerges from the punctum and expand outward during delivery, while the a memory frame and/or occlusion membrane convert from a constrained form to an expanded form in the canaliculus since the shape of the memory frame and or occlusion frame in its expanded form is larger than the punctal os. In the event removal of a canalicular occlusive device is necessary, upward traction is applied to the fixation arms. This traction will be transferred from the fixation arms to the remaining elements of canalicular occlusive device. The memory frame and/or occlusive element will collapse to converting to a more linear configuration (or constrained form) when loaded into the delivery device. This self-collapsing mechanism helps minimize canalicular trauma and patient discomfort when the device is removed. Such a design moreover enables the end user to remove the device with ease at the slit lamp with microforceps, as an example.

Manufacturing of the memory frame and linear frame are easily automated. Strategies for automation include a method to facilitate rapid and reproducible coiling of the helix consisting of a mask with grooves (such as a microdrill bit) that can be mounted onto a device that allows rotation of the frame but otherwise holds it in one position in the x, y and z axis. In a simple embodiment, the device consists of a microdrill handle and bit affixed to bearings that are then held stationary by a vice. The shape memory metal is spooled within the grooves of the device and then an external clamp such as a hemostat is applied to hold the wire wound around the mask. With clamp in place the memory metal is then heat treated in order to reset the shape of the memory metal in a coiled configuration.

A memory frame of the present invention may be made of memory metal. A memory frame may be partially or fully covered by an occlusive element made of a biocompatible membrane, as an example. All components of a canalicular occlusion device of the present invention may be made of the same or different materials.

Canalicular Occlusion Device Delivery to a Subject

The canalicular occlusion device of this invention is designed to be held in a collapsed form when associated with the delivery device. In its deployed form, the memory frame is free to expand and thereby expands the attached occlusive element. In its expanded form the occlusive membrane is held approximate to the canalicular wall and substantially prevents fluid passage through the canalicular system. Prior to delivery, an occlusive membrane is held in an approximately linear form or constrained form. When a wire is inserted coaxially in the proximal portion of the cannula it pushes an occlusive device out of the lumen and thereby causes the memory frame to expand forming and creating an expanded form of an occlusive device. The expansion of the memory frame thereby causes expansion of an occlusive membrane into an expanded form. An occlusive element in it expanded form remains in the distal cannula after delivery.

The canalicular occlusion devices of the present invention are designed to adapt to all anatomy. Some subjects have very a short vertical portion of their canalicular system while other subjects have a canalicular system with very long vertical portions. Similar variations in anatomy can be found in the horizontal component of the canalicular system. A delivery device is able to provide an occlusion device having an occlusion element in a constrained form (i.e. stretched to a substantially linear form). Upon and/or during delivery the occlusive element of the present invention is able to gently expand into the canalicular system regardless of the anatomical variation as shown in FIG. 3 (i.e. expanded form of an occlusion device of the present invention). In addition, by choosing the appropriate final diameter of an expanded occlusion element on the distal portion of an occlusion device, the occlusive element will comfortably fasten the canalicular occlusion device within the canalicular system.

Lacrimal Canalicular Delivery System

Lacrimal canalicular Delivery Systems LCDS (LCDS) of the present invention were made to deliver canalicular occlusive devices of the present invention to a subject and more broadly to deliver many other implants, that may fit within a canaliculus (for example), of a subject. To date various strategies have been employed to deliver an implant to the punctal os, the entrance to the lacrimal canalicular space, but few devices have been described to deliver an implant deep within the canalicular space at a specific location. Conventional delivery devices described an introducing mechanism for a canalicular stents to treat nasolacrimal duct obstruction as well an introducer for a canalicular occlusion device. These strategies rely on the end user to manually insert the introducing mechanism at the proper depth within the canalicular space and further require manual insertion and removal of the introducing mechanism. The present invention describes various LCDSs with an additional integrated eyelid alignment platform that provides end-users a precise means of delivering a canalicular implant through the punctal os and in the canaliculus in specific X, Y and Z dimension or location. Moreover, some LCDS include a catheter to deliver an implant and have a retraction mechanism. The retraction mechanism removes the delivery catheter out of the canalicular system in a manner that can provide superior comfort to a subject while also helping to ensure the implant position is not disrupted by direct manipulation of the delivery catheter by the end-user. The LCDS of the present invention include many benefits such as: 1) universality so one device can be used to deliver an implant into any canalicular system; 2) easily inserted and easily retrievable from the canalicular space; 3) superior comfort and low profile 4) minimal tissue injury during insertion and retraction from the canalicular space 5) ability for precise delivery into the canalicular space as it relates to the punctal os and eyelid in X, Y and Z dimensions.

Suitable polymers used to make an LCDS of the present invention includes polynorbornene, polycaprolactone, polyenes, nylons, polycyclooctene (PCO), blends of PCO and styrene-butadiene rubber, polyvinyl acetate/polyvinylidenefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and combinations thereof. Other materials of the present invention include memory metals including stainless steel, cobalt, nickel, chromium, molybdenum titanium, nitinol, tantalum, platinum-iridium alloy, gold, magnesium, or combinations. The intracanalicular component of the LCDS may have a rigidity in the range of 1 kPa to 10 kPa. Regarding an LCDS having an intracanalicular catheter, the width of the intracanalicular catheter may range from 0.1-10 mm and length of 1 mm to 10 mm, as an example.

An LCDS of the present invention may comprise a handle attached to an intracanalicular retractable catheter comprising a spring-based mechanism to push or retract an intracanalicular implant in and out of a canalicular space. Some LCDSs may further comprise a retaining member. In such embodiments, the donut shaped retaining member holds the spring in a compressed position until pushed centrally into the handle thereby allowing the spring attached to the intracanalicular catheter to move through the center of the donut shaped retaining member. An eyelid alignment platform ensures an implant, such as a canalicular occlusion device, is delivered in the correct X, Y, and Z dimensions in relation to the punctal os, lower canaliculus, or the upper canaliculus.

Figure 9A:
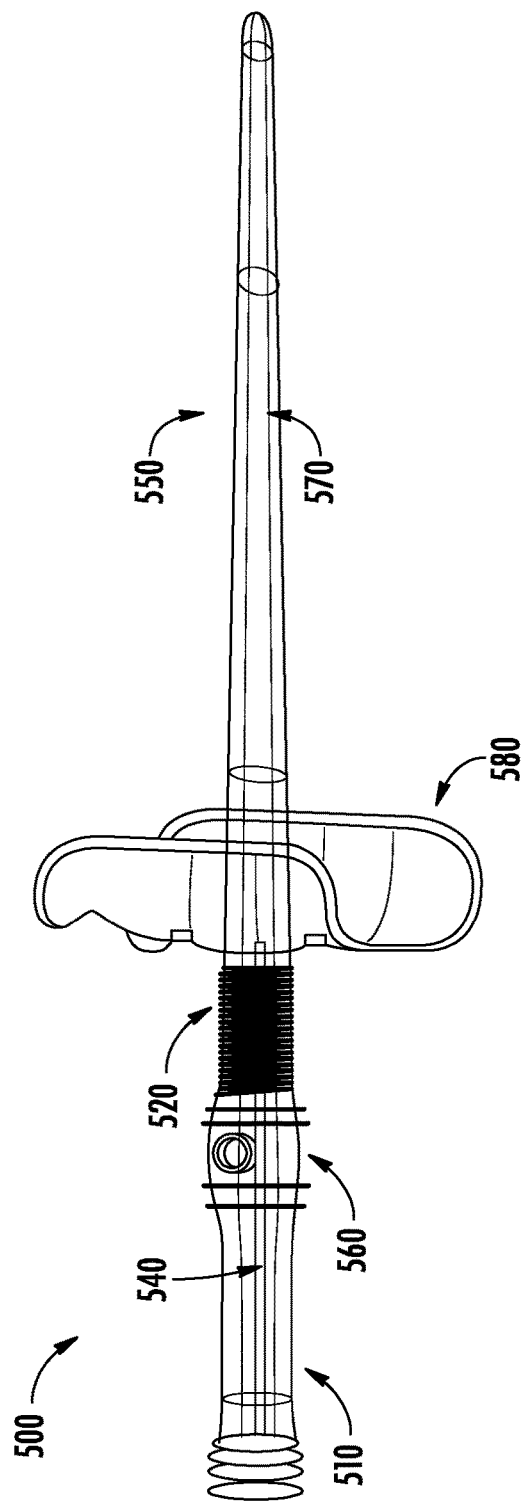
FIG. 9 illustrates an example of delivery catheter with plug prior to delivery.
Figure 9B:
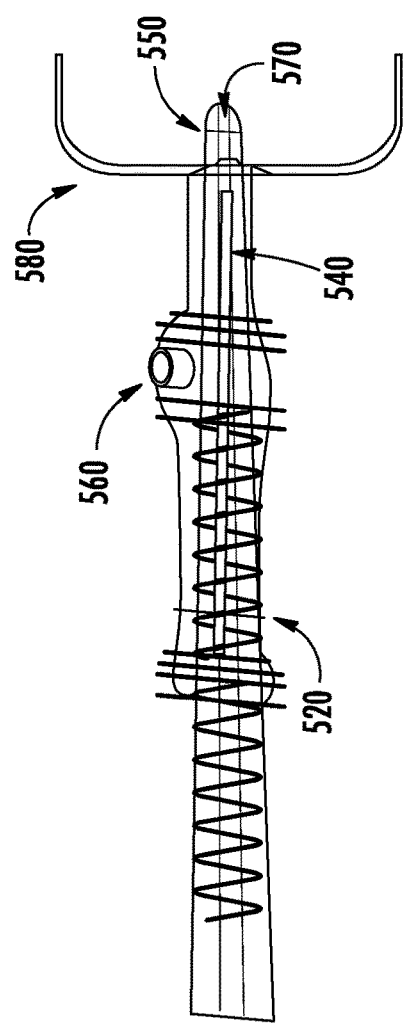
Figure 10:
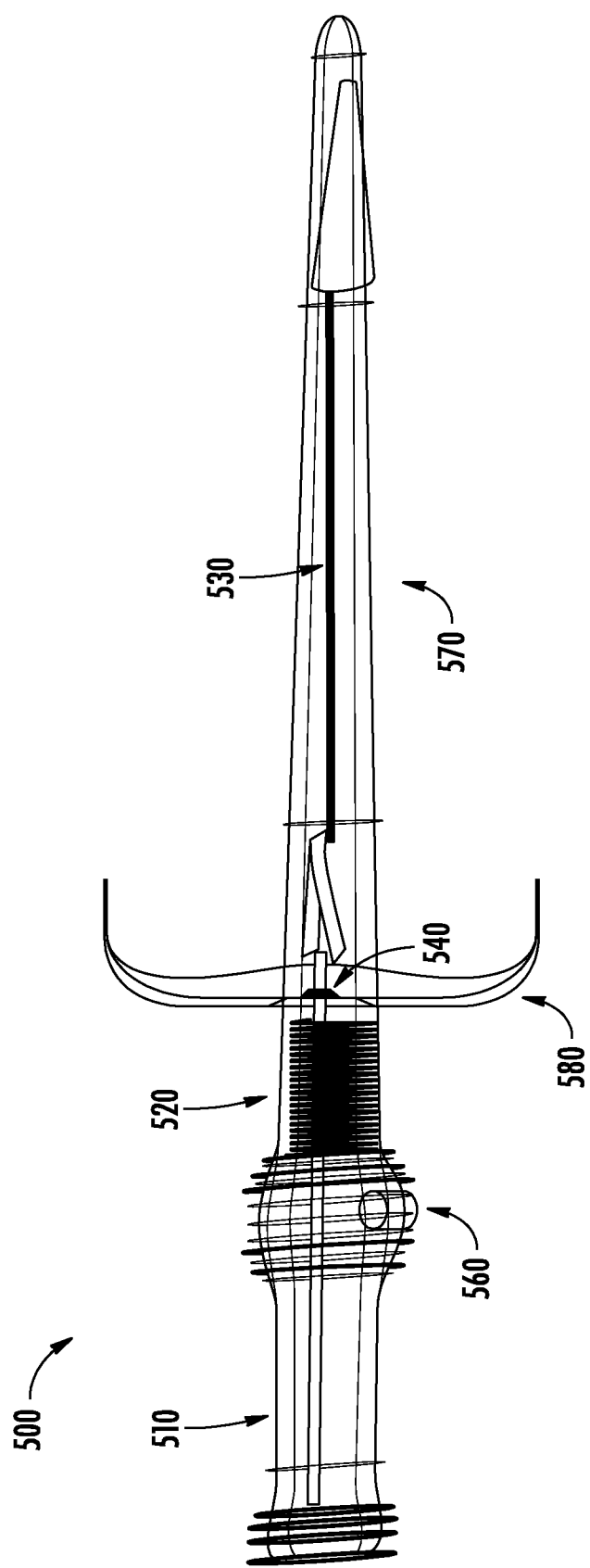
FIG. 10 illustrates a delivery catheter design deployment mechanism involving a donut shaped retaining member that holds a spring in compressed position until pushed centrally into handle thereby allowing the spring attached to the catheter to move through the center of the donut.

As shown in FIG. 10, one embodiment of a LCDS 500 of the present invention is loaded with a canalicular implant, such as a canalicular occlusive device 530. When a canalicular occlusion device having a memory frame in the shape of a helix 530 is loaded within the catheter, the helical frame of the canalicular occlusion device 530 is held in a linear configuration as shown in FIG. 10. The LCDS 500 has a low-profile design and maybe sold including a implant such as a canalicular occlusion device 530 (FIG. 10) or without an implant (FIG. 9).

FIG. 9 illustrates an LCDS in two forms, retracted and unretracted. As shown in FIG. 9, components of a LCDS 500 include a handle 510 that consists of a doughnut shaped retaining member including a deployment button 560 in some embodiments. The handle 510 is contiguous with the eyelid alignment platform 580 which enables precise positioning of a canalicular occlusive device in relation to the punctal os. Contained within the handle 510, is a sheath 550 through which the catheter 570 retracts. To facilitate retraction, sandwiched between the sheath 550 and the catheter 570 is a spring 520. The spring 520 is distally attached to the portion of the handle 510 contiguous with the eyelid alignment platform 580. The proximal portion of the spring 520 is attached to the proximal element of the catheter 570. When the catheter 570 is in open configuration, the spring 520 is maximally compressed as the proximal element of the catheter 570 and the distal portion of the handle 510 contiguous with the eyelid alignment platform 580 are in close proximity. When the catheter 570 is in its retracted form, the spring 520 is maximally expanded as the proximal edge of the catheter 570 and the portion of the handle 510 contiguous with the eyelid alignment platform 580 are no longer closely approximated. Prior to deployment, the catheter 780 is held emerging beyond the edge of the handle 510 with the spring 520 maximally compressed. The catheter 570 is held in this position by a deployment button 560 that precludes the catheter to move within the sheath 550. The deployment button 560 must have an element that extends within the lumen of the sheath 550. When the deployment button 560 is depressed, the retaining member 540 is removed from the lumen of the sheath 550 thereby enabling expansion of the spring 520 and catheter 570 within the handle 510 (unretracted form of an LCDS). To prevent migration of an implant within a catheter 570 into the handle 510, the lumen of the sheath 550 proximal to the canalicular occlusion device 530 contains a central pusher bar 540 that is held stationary in relation to the handle 510. This central pusher bar 540 is held affixed to the most proximal portion of the handle 510. Over this central pusher bar is threaded the sheath 550 that is similarly held fixated in position to the handle 510. Therefore, the catheter 570 retracts over this central pusher bar when retracting into the handle 510. The spring is compressed in FIG. 9A and where the spring is expanded in FIG. 9B.

Figure 11B:
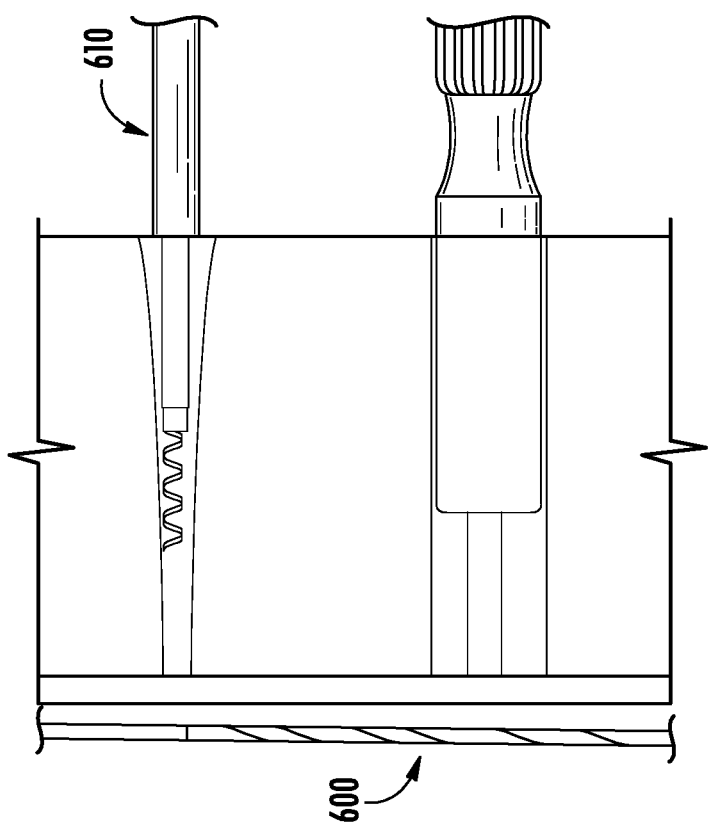
FIG. 11A-11B illustrates a prototype LCDS shown consisting of a stainless steel cannula and a coaxial guidewire that when threaded through the cannula through the proximal end acts to push an implant loaded a the intracanalicular element out of the cannula. In this example the delivered device is a canalicular occlusion device of the present invention.
Figure 11A:
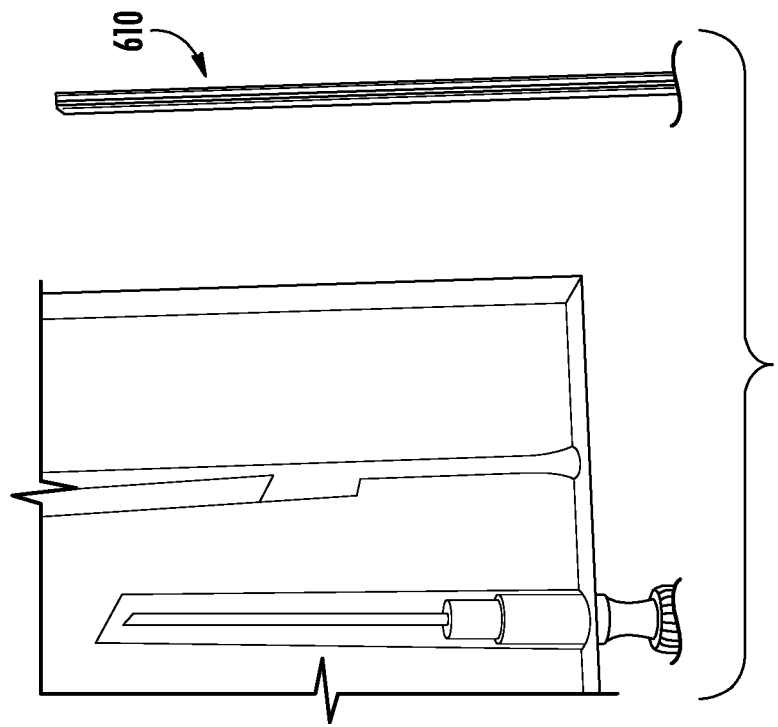

Another example of a LCDS is shown in FIG. 11 comprising a guide wire 600 and a delivery cannula 610. An implant, such as a canalicular occlusive device, electronic device or drug delivery device, is placed in a delivery cannula 610 and then pushed out into a canalicular system of a patient by the guide wire.

The preferred LCDS embodiment includes a flexible catheter. The flexible catheter is intended to remain around an implant, such as a canalicular implant, prior to deployment of the implant. Upon deployment of an implant, the flexible catheter will retract into a cylindrical cavity in the barrel or handle of a LCDS. This can be mechanically facilitated by coupling a spring under pressure that is attached to the catheter and expands upward into the device once expanded. The catheter can be used to precisely position an implant at an implantation site as well as participate in deployment of an implant at the implantation site. Some catheters have guidewires running their length to aid in positioning and deployment of an implant. As an alternative to the guidewire, a catheter may be coaxial with an inner sleeve running inside the length of the catheter. The inner sleeve is used to hold an implantable medical device in position while the outer catheter is pulled, causing deployment of the device. Handles, knobs, or other manually operated control means are attached to the opposite end of the catheter in this assembly.

In another embodiment, the present invention is a deployment system for a self-expanding endoluminal device comprising a self-expanding endoluminal device at least partially enclosed by a removable sheath, and a deployment line integral with the sheath, wherein the sheath is convertible to the deployment line as the sheath is removed from the endoluminal device.

In certain embodiments, LCDS of the invention include a housing having an elongated intracanalicular element, a deployment mechanism at least partially disposed within the housing, and a hollow shaft coupled to the deployment mechanism, in which the shaft is configured to hold an intracanalicular implant. The housing of devices of the invention may include a proximal portion and a distal portion. In certain embodiments, the distal portion of the housing is movable within the proximal portion of the housing. The housing may further include a member that limits axial retraction of the distal portion of the housing.

LCDS of the invention may be completely automated, partially automated, or completely manual. LCDS of the present invention may be connected to larger robotic systems or may be used as stand-alone handheld deployment devices. In particular embodiments, the device is a handheld device. In some embodiment, LCDS may include an indicator that provides feedback to an operator as to the state of the deployment mechanism. The indicator may be any type of indicator know in the art, for example a visual indicator, an audio indicator, or a tactile indicator. In certain embodiments, the indicator is a visual indicator.

LCDS Delivery and Expansion Methods

LCDS used are used in method to delivery one or more implants to a canalicular space. The implants may be used to occlude a canalicular space, provide electrical stimulation to a canalicular space wall or provide a pharmaceutical agent to treat disease. Typical eye disease treated by using an LCDS include dry eyes, glaucoma, or other ocular conditions requiring topical ocular medications. As mentioned, LCDS deliver implants to a precise X, Y and Z dimension within a punctal os, a lower canaliculus, an upper canaliculus, or a common canaliculus. Occluding the canaliculus at an appropriate depth with an implant delivered by a LCDS will result in a reservoir of tears proximal to the occlusion. If a LCDS delivers an implant that is a drug delivery system, for example a depot drug delivery system, the implant may be designed to occlude a canaliculus and also administer a drug. When a subject blinks, a drug administered by an implant comes in contact with tears by the contracting of Mueller's muscle. A drug delivery implant is administered into a canaliculus of a subject, having or prone of getting dry eyes, glaucoma or another ocular condition. The drug delivery implant results in treating or preventing that condition in the subject when compared to a reference subject that has been administered an implant. More specifically, part of the LCDS, such as the catheter part, is advanced into the canalicular system of a subject through the punctal os. When administering an implant into the canalicular system of a subject using a LCDS, the implant may terminate prior to the common canaliculus thereby occluding one punctum. Alternatively, the device may deliver the implant into the common canaliculus thereby occluding the upper and lower punctum.

LCDS of the present invention may be used to deploy an expandable endoluminal device. In preferred embodiments, the endoluminal device is self-expanding as a consequence of the device design and the materials used to construct the device. In other embodiments, the endoluminal device is expanded with an inflatable balloon placed within the device. The endoluminal device is maintained in a compacted, or collapsed, configuration by a removable sheath. The sheath is removed from around the endoluminal device by pulling on a deployment line. The deployment line is an integral, continuous, extension of the sheath that is made of the same material as the sheath. As the deployment line is pulled, the sheath progressively retracts from around the endoluminal device and also functions as an extension of the deployment line. When the sheath has been substantially removed from around a portion of the endoluminal device, that portion of the endoluminal device is free to expand. Removal of the sheath may be continued until the entire endoluminal device is freed from radial constraint. The deployment line, along with any remaining sheath material, may be removed from the implantation site through the use of a catheter used to deliver the sheathed endoluminal device to the site. Other implants used in the present invention include some implantable medical devices, such as stents, stent-grafts, or other endoluminal devices. These implants often require reconfiguration from an initial constrained form to an expanded cylindrical configuration as the device is deployed at an implantation site. These devices can expand on their own by virtue of the design and composition of their structural elements or through the use of an inflatable balloon placed inside the devices.

Implants such as self-expanding endoluminal medical devices are maintained in a compacted configuration in a variety of ways. Some devices are maintained in a compacted configuration by simply confining the compacted devices inside a catheter, or similar tool. Other devices are placed inside a sheath following compaction. In these assemblies, a control line is often used to assist in releasing the endoluminal device from the sheath.

A LCDS comprising a canalicular occlusion device may be used in delivery methods. In one example an LCDS includes a catheter and the canalicular occlusion device is loaded within catheter. The catheter of the LCDS is of such a profile that for canalicular occlusion device comprising a memory material frame in the shape of a helix to enter a device it must assume an uncoiled or a linear formation ("constrained" form). A suitable LCDS for delivering this type of implant typically comprises a handle in which the catheter retracts. Affixed to the handle of an LCDS is an eyelid speculum that is designed to sit on the lid margin once the catheter has been threaded through the punctal os into the canalicular system. Loaded within said catheter is the canalicular occlusion device in a constrained form. A suitable LCDS includes a catheter retraction assembly and delivery methods of the present invention may include the use of a speculum. The LCDS catheter is capable of delivering the helix canalicular occlusion device precisely within the canalicular system in order that the distal end of the catheter just emerges beyond the punctal os. This is accomplished by holding the canalicular occlusion device in its constrained form in the proper proximal to distal orientation as well as in proper orientation in regards to the lid margin as described below.

The LCDS of the current invention is designed to be low enough profile to enable its introduction into the canalicular space when it is free of or contains an implant. When an LCDS contains an implant, the implant becomes almost narrow (almost linear if the implant is a canalicular occlusive device having a helical frame that is stretched) prior to delivery of the implant to a subject. When the catheter element of the LCDS retracts, the plug is free to expand to its native shape, for example based upon its predetermined shape memory metal conformation. As the canaliculi measure 8-10 mm in length and 0.5-1.0 mm in diameter the ideal canalicular LCDS dimensions (free or contain and implant) would fall within these bounds, for example in the range of 5-12 mm in length and 0.3 and 2.0 mm in width. An implant may be delivered far in the canaliculus of a subject with an LCDS having long enough dimension to reach the common canaliculus. The LCDS may then deliver an implant into the common canaliculus providing occlusion of the upper and lower punctum with a single device.

The geometry of the human canalicular system will dictate the optimal design of the LCDS. In an ideal embodiment, the intracanalicular portion of the LCDS would be low-enough profile to facilitate ease of introduction through the canalicular system into the punctal os without the need for dilation. In the event dilation is necessary, it is critical that the intracanilicular portion of the LCDS does not damage the wall of the canalicular system. In the case of a LCDS having a mechanically retractable catheter, the intracanilicular portion of the LCDS must be low enough profile to not engage the wall of the canalicular system thereby creating friction. In addition to a low profile, the intracanalicular portion of the LCDS may consist of a material that is free of surface irregularities and having a smooth surface that is unlikely to engage the canalicular wall, or the implant, to be delivered. Moreover, the material of the intracanalicular portion of the LCDS may be lubricated by direct application of a lubricant such as hydroxypropylmethylcellulose 2.5%, Goniosol GONAK or other medical lubricants. To ensure delivery of the implant into a sterile environment the lubricant may contain antiseptic such as chlorhexidine gluconate as is the case with Surgilube. Moreover, it may contain an anesthetic such a lidocaine or lignocaine similar to the traditionally used Lignocaine gel. This may be provided in a kit with the LCDS for the end-user to directly coat the intracanalicular portion of the LCDS or the intracanalicular portion of the LCDS may come prelubricated and kept in a water and airtight seal to keep the device sterile and prevent dehydration of the lubricant. In addition to a topical lubricant, the intracanalicular portion of the LCDS may be chemically surface modified to ensure the material will not create friction with the canalicular anatomy or the implant to be delivered. Depending upon the implant, surface modification of the intracanalicular portion of the LCDS may consist of hydrophobic or hydrophilic modifications. Such modifications may be applied to the LCDS and the implant alike. In addition to reducing friction they may also act to decrease the chance of bacterial biofilm formation. As is known to those well-versed in the art, hydrophilic coating technologies make polymeric devices susceptible to fluids by grafting polymers into covalent bonds to create-water attracting surfaces. Hydrophilic molecules are polar and ionic, which make them lubricious, abrasion resistant and non-thrombogenic. The water retention and lubricity characteristics of hydrophilic coatings reduce the friction that medical devices impart during interventional procedures. These modifications have been extensively explored in the intravascular space to decrease the force required to manipulate intravascular devices during interventional procedures. They can decrease the frictional force between 10 to 100-fold and help reduce the trauma to the vessel wall. In a similar way, these modifications when applied to this invention may reduce the friction with the canalicular anatomy as well as the delivered implant.

In contrast, hydrophobic coatings may be applied to components of the present invention including implants and LCDS. Hydrophobic coatings are nonpolar repellants that can greatly reduce risks of contamination and infection in patients. For example, the addition of a hydrophobic coating to an implant will create a hydrophobic coating on its surface and will enhance resistance to biofilm development. A biofilm is a composition comprising a biological organism such as bacteria. Hydrophobic coatings also create surfaces on implants that are water-repellant, self-cleaning, antifouling and/or anticorrosive effects.

Eyelid Alignment Platform

An eyelid alignment platform of an LCDS may having a suitable design for aligning an LCDS on a punctal os. For example, an LCDS may be delivering an implant such as an occlusion device of the present invention having fixation arms in the shape a T. In this case, an eyelid alignment platform may have a horizontal component to align the T shaped fixation arms in parallel with the lash line to improve patient comfort.

Lacrimal canalicular delivery devices (LCDS) of the invention accomplish intracanalicular implant deployment without use of an optical apparatus. LCDS have a biased distal portion, such that upon entry of the distal portion of the device into an anterior chamber of an eye, the distal portion slides to fit within the anterior chamber angle of the eye. An eyelid alignment platform of the device informs an operator that the deployment device is properly positioned for proper placement of the intracanalicular implant within the eye.

LCDS Delivery and Retraction Methods

As shown in FIG. 10B, and LCDS is retracted, typically during delivery. Once the catheter is fully retracted, an implant contained within the body or lumen of the catheter is freed and converts to an expanded form. If the implant is a canalicular occlusion device comprising fixation elements in the shape of T shaped arms, then the T shaped arms are free to expand attaching the implant by the fixation elements to the edge of a punctum.

During LCDS delivery a speculum may be used. When a speculum is used during LCDS delivery, then in order to enable collapse of the T arms, the speculum will inherently need a small vaulted area in relation to lid margin allowing room for the T arms to freely swing open and expand. An additional means or ensuring proper directionality can be achieved by making this vaulted area of the speculum a slot that is aligned parallel to the lash line. After a catheter of a LCDS is retracted and an implant is deployed, the LCDS and speculum can be removed from the lid.

In certain embodiments, the retraction mechanism can be manual in which the end user holds the LCDS against the lid and retracts the catheter with a lever thereby pulling the catheter within the LCDS. In a preferred embodiment, this retraction mechanism is mechanical. Through use of a spring that coils around the catheter and then affixing the ends of the spring to the proximal catheter tip and also the housing of the speculum, a downward force on the catheter will cause the spring to collapse. By employing a button attached to a lever that holds the catheter and spring in a collapsed position with catheter emerging beyond the speculum, when said button is pushed thereby releasing the lever, the spring is free to expand thereby pulling the catheter within the body of the LCDS.

To prevent premature deployment (or retraction of a catheter of a LCDS) a variety of mechanisms can be employed. One embodiment that both protects the button from being pushed as well as the delicate catheter and implant inside the catheter from being damage is that a LCDS comprises a rigid cap or sheath. The cap or sheath encases the catheter and emerges up and over the button and clips to the housing of the LCDS and above a speculum if used. End user would then just remove this cap, thread the catheter into the punctum until the speculum rests on the lid margin in proper orientation. By pushing the deployment button, the implant would then expand in proper orientation. Such setup is similar to a self-retracting needle system found in IV access products. Examples include BD Angiocath™- and and Autoguard™ shielded iv catheter. Instead of needle being retracted, the catheter is being retracted in the present invention.

In certain embodiments, the deployment mechanism may include a two-stage system. The first stage is a pusher component and the second stage is a retraction component. Rotation of the deployment mechanism sequentially engages the pusher component and then the retraction component. The pusher component pushes the intracanalicular implant to partially deploy the intracanalicular implant from within the shaft, and the retraction component retracts the shaft from around the intracanalicular implant. The deployment mechanism further includes at least one member that limits axial movement of the shaft.

Convention delivery devices used to delivery punctal plugs, unlike LCDS of present invention, do not utilize a control line that is integral with a confining sheath. Nor do conventional delivery devices feature a sheath that is convertible to a control line as the sheath is removed from around the endoluminal device. Such an integral control line and confining sheath would preferably be made of a continuous thin-walled material or composite thereof. The thin-walled material would be flexible and exert minimal restrictions on the flexibility of an underlying endoluminal device. Thin-walled materials would also reduce the profile of the sheath and endoluminal device combination. An integral control line and confining sheath would simplify manufacture of control line-sheath constructs by eliminating the need to mechanically attach the control line to the sheath. An integral control line and confining sheath would also eliminate concerns regarding the reliability of the mechanical attachment of the control line to the sheath.

The removable sheath is made of one or more thin, flexible polymeric materials including composites thereof. The sheath ordinarily assumes the form of a continuous thin-walled tube when constraining an endoluminal device. Such a thin-walled sheath exerts minimal resistance to longitudinal flexing of an underlying endoluminal device. The thin-walled sheath also reduces the profile of the sheath-endoluminal device combination, when compared to conventional constraints. In preferred embodiments, a double-walled tubular sheath is used. Double walls enable the sheath to be retracted from around an endoluminal device by rolling or sliding one wall past the other wall. As the sheath is retracted in this manner, the sheath portion does not rub or scrap against the endoluminal device. This is particularly advantageous when coatings containing medications or pharmaceuticals are placed on surfaces of the endoluminal device that may be removed by a sheath that rubs or scrapes against the endoluminal device during removal.

The deployment line is formed from the same material as the tubular sheath and is an integral extension of the sheath material. The deployment line extends from the sheath through a delivery catheter to a control knob located at the proximal end of the catheter. Pulling on the control knob actuates the deployment line. Once the deployment line is actuated, the removable sheath begins to retract from around the endoluminal device.

In one embodiment, as removed sheath material travels beyond the receding end of the sheath, the sheath begins to become converted to deployment line. Conversion of the sheath into the deployment line usually begins at a point where the tubular sheath breaks apart, separates, and converges into deployment line material. In preferred embodiments, means are provided for initiating or sustaining the conversion of the sheath to deployment line. These means may take the form of perforations, stress risers, or other mechanical weaknesses introduced into the sheath material. The means can also be cutting edges or sharp surfaces on the delivery catheter.

In preferred embodiments, materials and/or composites exhibiting compliance, compressibility, and/or resilience are placed between the endoluminal device and the delivery catheter. The compliant material serves to cushion the endoluminal device when constrained by the sheath and may assist in expansion of the device when unconstrained. The compliant material also serves to anchor and retain the endoluminal device in place on the underlying catheter shaft. When used in combination with a double-walled sheath, the compliant material can have tacky surfaces that further assist in anchoring and retaining the endoluminal device. In these embodiments, the tacky surface of the compliant material does not interfere with removal of the sheath from around an endoluminal device. The anchoring of the endoluminal device via the compliant material eliminates the need for barrier, or retention means at either end of the endoluminal device. The absence of barrier means also contributes to a reduction in the profile and an increase in flexibility of the distal portion of the assembly. The present invention can also be provided with an additional catheter or catheter lumen for the deployment line in order to prevent the deployment line from leaving the general path established by the delivery catheter.

Accordingly, one embodiment of the present invention is a deployment system for a self-expanding endoluminal device comprising a removable sheath adapted to cover the endoluminal device, the sheath comprising a thin continuous film adapted to surround at least a portion of the endoluminal device and constrain the device in an introductory profile, wherein the deployment system includes a deployment line integral with the sheath to effectuate device deployment, and wherein upon deployment, the sheath separates from the endoluminal device through actuation of the deployment line, the sheath becoming removed from the device along with the deployment line.

Canalicular Occlusion Device Removal from a Subject

A canalicular occlusion device without fixation arms or linear frame is deployed within the canalicular system and maybe retrieved from a subject using a removal device that is inserted into the canalicular system and attaches to the canalicular device. A canalicular occlusion device that does not include a fixation element or linear frame maybe retrieved from a subject using a removal device that remains outside the punctal os and is able to attach to a fixation element. Suitable removal devices used in the present invention include microforceps, nitinol loops or any other device that may be inserted into the canalicular system and attach to a canalicular occlusion device of the present invention. In an ideal design, the removal device should be low profile and of the right flexibility to easily thread into the canalicular or, adjoin a canalicular occlusion device of the present invention, engage (or attach to) the device. Tension is applied to the removal device so as to remove a canalicular occlusion device from the canalicular system of a subject.

An inclusion device of the present invention may be designed to enhance recovery. For example, fixation elements may be made in the shape of one or more hoops, or a helix to engage a removal device. The memory frame element may have a portion in which no sheet of PTFE connects the adjoining loops of nitinol coil. The memory frame may be a helix and the diameter of said neighboring loops can be varied in order to enable engagement of the helical frame by the removal device.

Figure 5A:
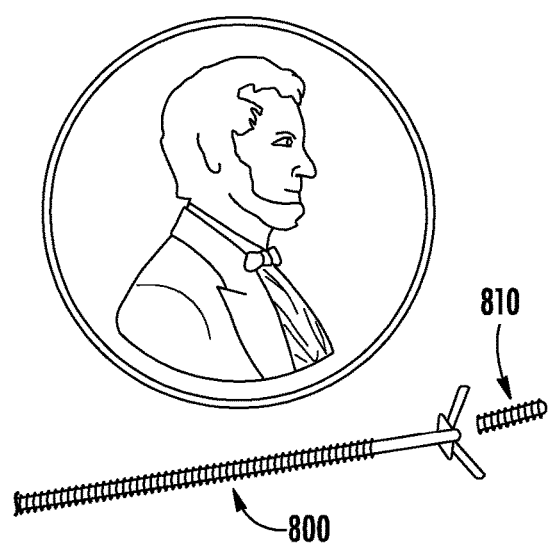
FIG. 5A-5D illustrates a prototype helix device shown with a penny for relative size deployed into an acrylic canalicular model and recovered with flexible shaft microforceps.
Figure 5B:
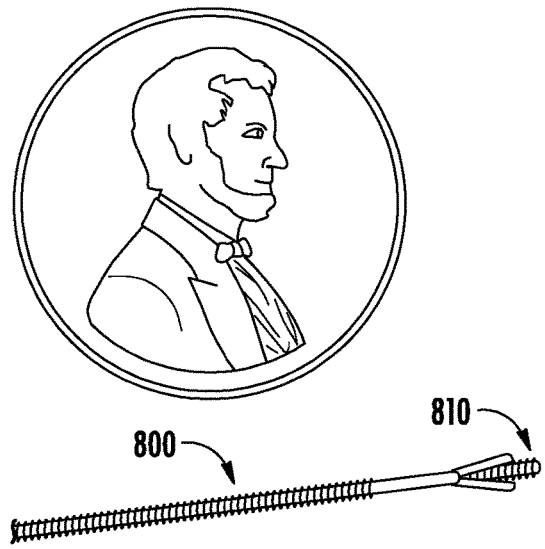
Figure 5C:
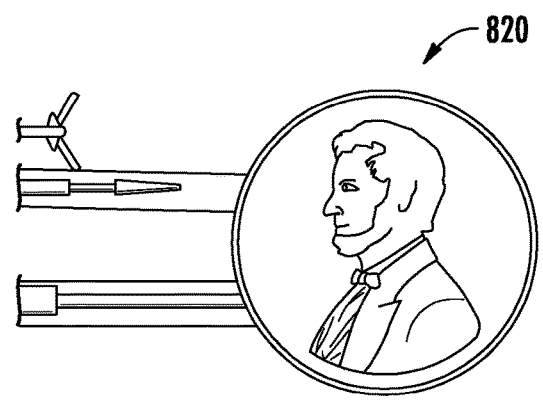
Figure 5D:
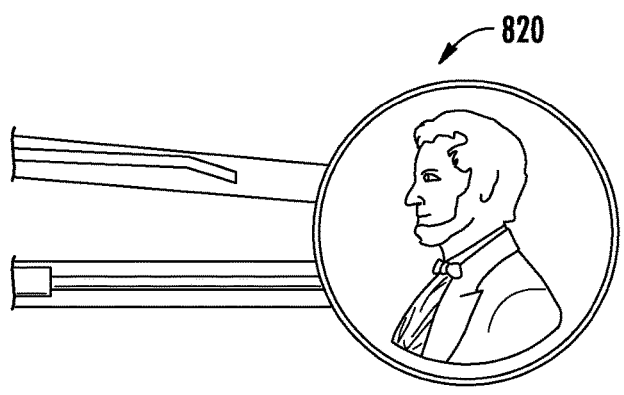
Figure 6A:
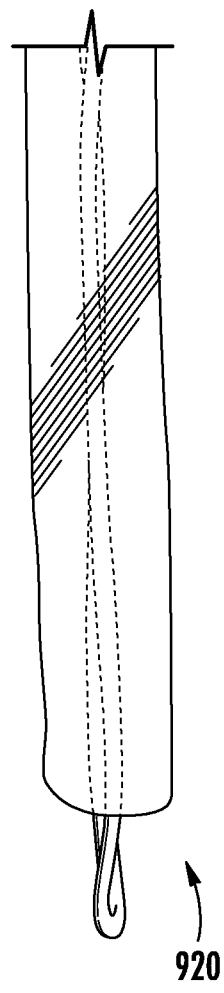
FIG. 6A-6C illustrates a nitinol capture loop opening from within catheter.
Figure 6B:
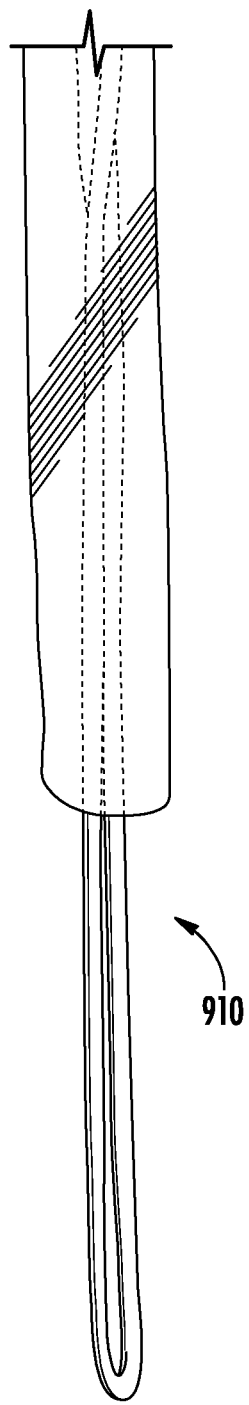
Figure 6C:
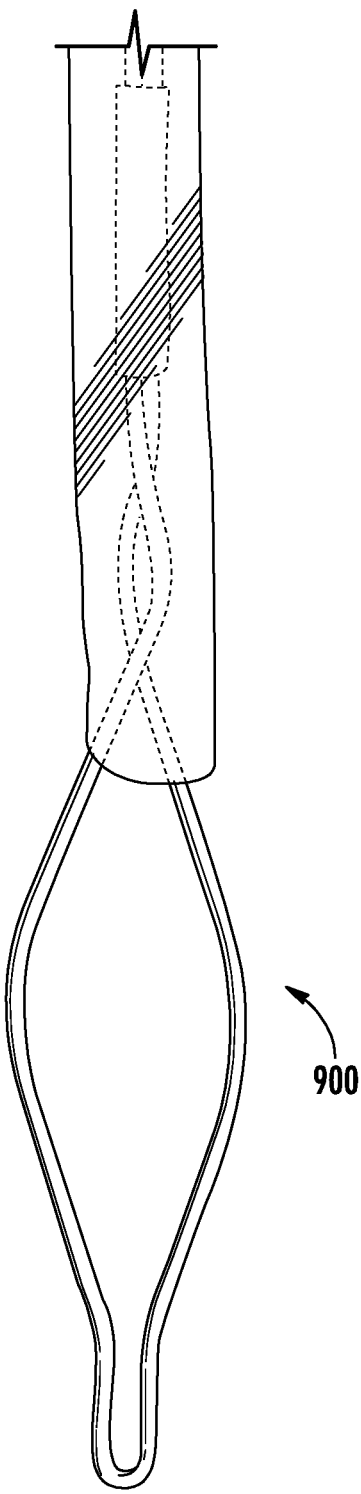

An example of a removal device includes a microforcep 800 (FIG. 5) that are able to attach to a prototype occlusion device 810 in a model canalicular system 820 as shown in FIG. 5C. The removal device will pull on an occlusive device of the present invention an remove it from the canalicular system. The removal device, such as microforceps 800, may attached to any location of an occlusive device for retrieval of a canalicular occlusive memory device from the canalicular system. For example, a removal device may attach a fixation element in the shape of arms 408, as an example. Other times a removal device may attach to an occlusive device of the present invention at other locations such as at the memory material frame area, and/or the occlusive element area as examples. Applying pressure to the removal device while it is attached to an occlusive device of the present invention causes an occlusive device of the present invention to straighten out and take a constrained form while in the canalicular system during removal. The removal of a stretched occlusive device (i.e. in a constrained form) from a subject results in minimal trauma or tissue damage during removal of the occlusive device. Other examples of removal devices include those embodiments illustrated in FIG. 6A-C. A removal device in the shape of an open loop 900 is ready to attach an occlusion device of the present invention located in a canalicular system of a subject. A removal device in the shape of a closed loop 910 illustrates how a delivery device will enter a canalicular system of a subject. A removal device in a sheath 920 illustrates a removal device surrounded by a sheath prior to the removal of an ocular device.

EXAMPLES

Example 1: Occlusion

Figure 7A:
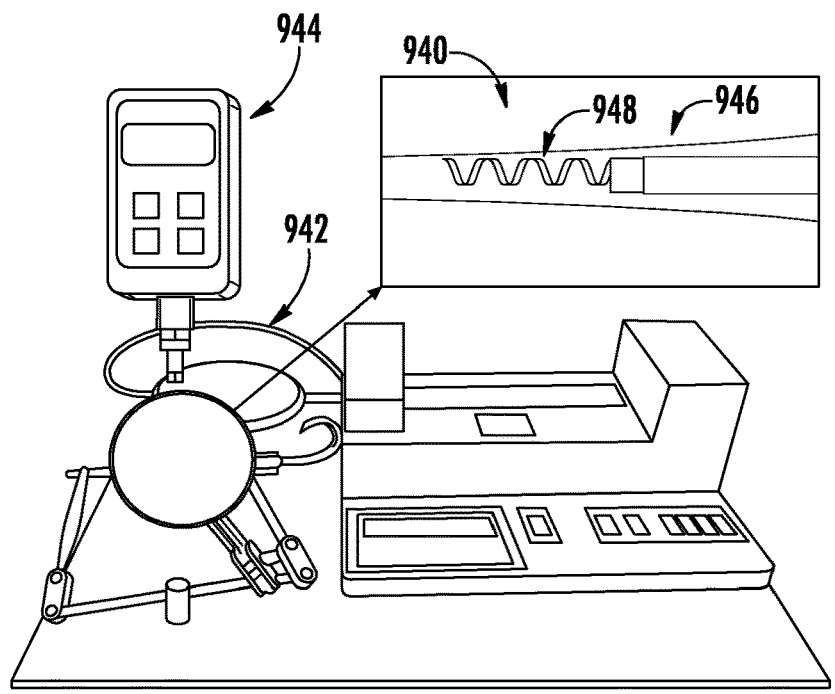
FIG. 7A-7B illustrates an occlusion testing system including an acrylic model 940 with a cylinder space 946. (A) The acrylic model 940 is attached to a syringe pump elastomeric tubing 942 and pressure gauge 944. Pressure is increased in the cylinder space 946 of the acrylic model before and after the cylinder space 946 is plugged with a second prototype occlusion device 948 of the present invention. (B) The graph demonstrates two results obtained from placing a second prototype occlusion device 948 in the cylinder space 946. First, the pressure at which the second prototype occlusion device 948 fails to occlude in the cylinder space 946 (the cylinder space is a model for a canalicular space) was determined as represented as an asymptote of graph. Second when the prototype occlusion device 948 was removed, complete reversibility of occlusion was observed as the latter pressure falls to zero after removal of prototype occlusion device 948.
Figure 7B:
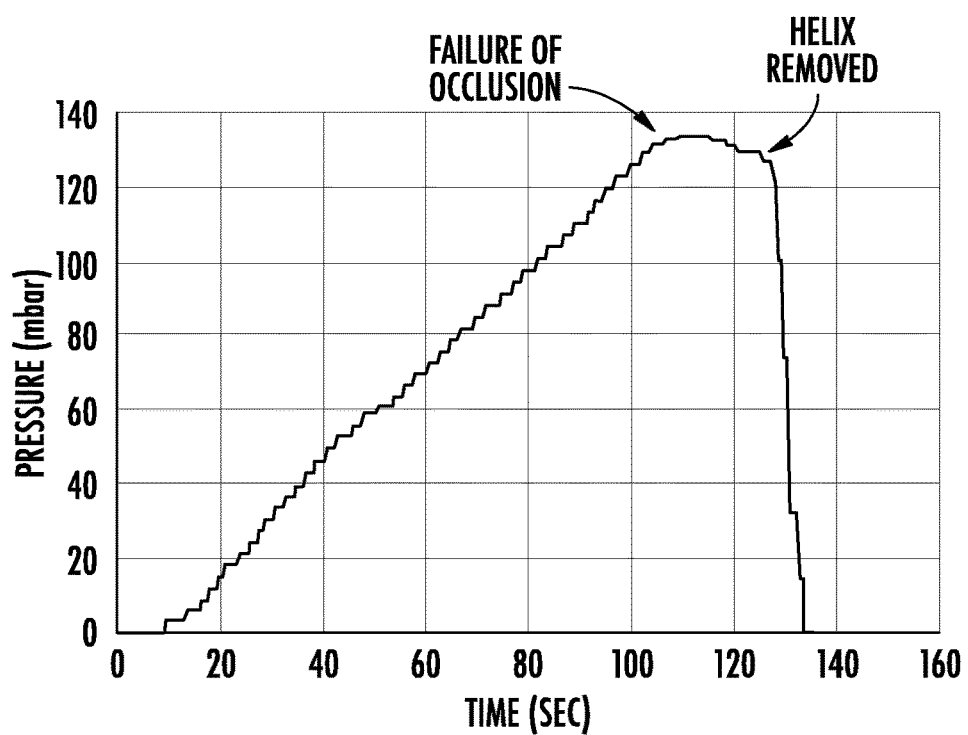
Figure 8C:
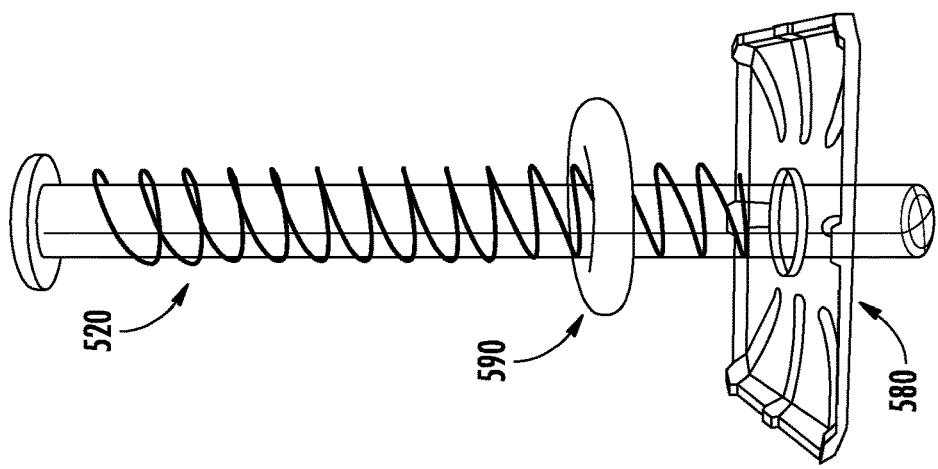
FIG. 8A-8C illustrates a model delivery catheter.
Figure 8B:
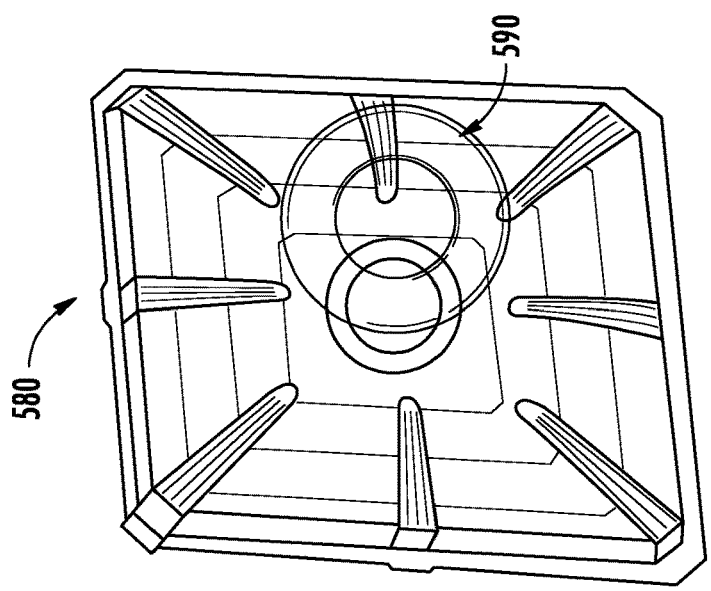
Figure 8A:
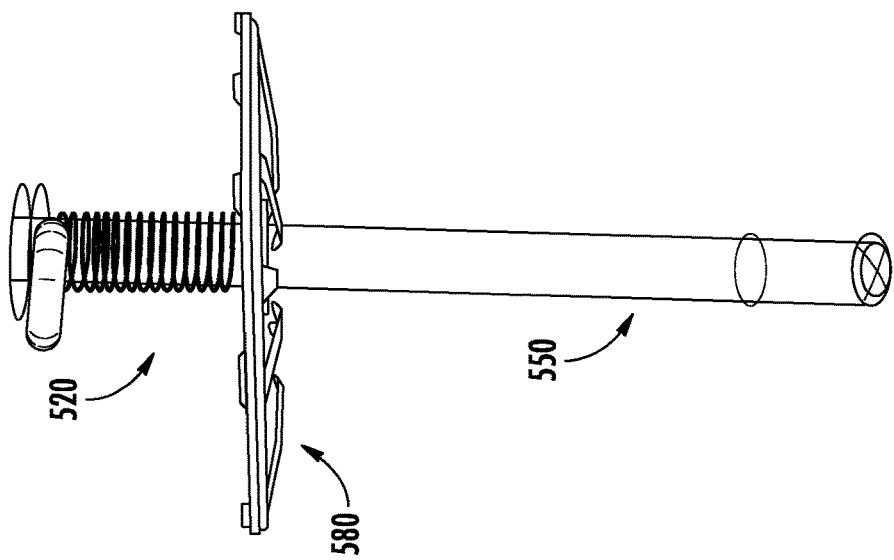

FIG. 7 illustrates an occlusion testing system consisting of an acrylic model 940 attached to a syringe pump elastomeric tubing 942 as well as a pressure gauge 944 thereby enabling measurement of the resulting pressure change in the acrylic model 940, more specifically the cylinder space 946 before and after occlusion of the cylinder space 946 with second prototype occlusion device 948. A red arrow points to an illustration providing a view within an acrylic model 940 of a prototype second prototype occlusion device 948 being deployed. In this example, the second prototype occlusion device comprises heat shrink PTFE applied over a Cook commercial aneurysm coil. The helical structure of the second prototype occlusion device 948 is seen as it is pushed with non-floppy end of guidewire through deployment into the cylinder space 946. FIG. 7b illustrates a graph having pressure units on the Y axis versus time units on the X axis. Once a second prototype occlusion device 948 is deployed in the cylinder space 946, the pressure is increased. The pressure is allowed to build up behind the second prototype occlusion device 948 until the second prototype occlusion device fails to occlude in the cylinder space 946 allowing air to escape around the second prototype occlusion device 948. In addition, when a second prototype occlusion device 948 is removed from the cylinder space 946 using microforceps, the pressure falls to zero within the cylinder space 946. The testing system has demonstrated that, the second prototype occlusion device 948 fails to occlude the cylinder space 946 when the pressure behind the second prototype occlusion device is in the range of 121 to 141 mbar. The helix was capable of withstanding 131.25+/−10.37 mbar (n=47) before allowing air to escape around the device (i.e. when graph reaches peak pressure as shown in FIG. 7b). Following occlusion failure, the second prototype occlusion device 948 is removed showing a rapid return to zero pressure illustrating complete reversible occlusion. With the inherent limitations of an acrylic model 940 being made of relatively solid material, further in vivo work is required to determine the optimal outward radial force of an inclusion device of the present invention. Such force may be modified by changing: the number of coils, gauge of the wire, diameter of the coil and the materials used to make an occlusive device of the present invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A lacrimal canalicular delivery system comprising:
   a sheath;
   a catheter movably disposed within the sheath;
   an eyelid alignment platform;
   a handle connected to the catheter; and
   a spring wherein the spring is disposed between the sheath and the catheter and wherein the spring is distally attached to a portion of the handle that is contiguous with the eyelid alignment platform and wherein a proximal portion of the spring is attached to a proximal element of the catheter.

2. The lacrimal canalicular delivery system of claim 1 wherein the catheter is open when the spring is maximally compressed.

3. The lacrimal canalicular delivery system of claim 1 wherein the catheter is retracted when the spring is maximally expanded.

4. The lacrimal canalicular delivery system of claim 1 wherein the catheter defines a lumen and wherein an implant is disposed within the lumen.

5. The lacrimal canalicular delivery system of claim 4 wherein the implant is selected from the group consisting of a canalicular occlusive device, an endoluminal device, depot drug, drug, an electric stimulation device, and a combination thereof.

6. A method of delivering an implant to a canaliculus of a subject comprising the steps of:
   providing a lacrimal canalicular delivery system of claim 4;
   aligning the eyelid alignment platform on an eyelid of a subject over the puntal os; and
   administering the implant into the canaliculus of a subject by applying force to the catheter.

7. The method of delivering an implant of claim 6 wherein the implant is selected from the group consisting of a canalicular occlusive device, an endoluminal device, an electric stimulation device, a depot drug delivery device, a drug and a combination thereof.

8. The method of delivering an implant of claim 6 wherein the catheter extends through a punctal os into the canaliculus of the subject and the implant is released into the canaliculus when the catheter is retracted.

9. The method of claim 8 wherein the implant delivers a pharmaceutical agent and wherein the implant is released close to the punctal os so that the pharmaceutical agent elutes in tears of the subject.

10. The method of claim 8 wherein the implant delivers a pharmaceutical agent and wherein the implant is released deep in the canaliculus so that the pharmaceutical agent is prevented from eluting in the tears.

* * * * *